United States Patent [19]

McCain et al.

[11] Patent Number: 4,468,135
[45] Date of Patent: Aug. 28, 1984

[54] RETORT POUCH THERMAL SIMULATOR AND METHOD OF OPTIMIZING HEAT TRANSFER IN RETORT CONDITIONS

[75] Inventors: George R. McCain, Northbrook; Philip H. Blaetz, Barrington, both of Ill.

[73] Assignee: Kraft, Inc., Glenview, Ill.

[21] Appl. No.: 462,939

[22] Filed: Feb. 1, 1983

[51] Int. Cl.³ .................... G01K 1/02; G01K 13/00
[52] U.S. Cl. ........................... 374/44; 374/12; 374/29; 374/134; 422/26; 422/119; 422/88; 422/231
[58] Field of Search .................. 374/12, 43, 107, 29, 374/44; 99/342; 422/26, 297, 119; 426/88, 231

[56] References Cited

U.S. PATENT DOCUMENTS

| | | | |
|---|---|---|---|
| 1,729,298 | 9/1929 | Stewart | 374/190 |
| 3,194,071 | 7/1965 | Hager, Jr. | 374/134 X |
| 3,690,175 | 9/1972 | Butts | 374/134 |
| 3,754,465 | 8/1973 | Romito et al. | 99/342 |
| 3,769,932 | 11/1973 | Romito et al. | 116/216 |
| 3,812,716 | 5/1974 | McIntyre | 374/110 X |
| 3,960,670 | 6/1976 | Pflug | 422/26 X |
| 3,964,313 | 6/1976 | Connick | 374/110 X |
| 4,024,751 | 5/1977 | Potrzebowski | 374/43 |
| 4,095,982 | 11/1977 | Bowman | 374/44 |
| 4,195,061 | 3/1980 | Kalasek | 422/297 X |
| 4,263,258 | 4/1981 | Kalasek | 422/26 X |
| 4,293,916 | 10/1981 | Del Re | 374/134 X |
| 4,340,610 | 7/1982 | Nloras | 426/88 |

*Primary Examiner*—Daniel M. Yasich
*Attorney, Agent, or Firm*—Fitch, Even, Tabin & Flannery

[57] ABSTRACT

A device is provided which simulates heat transfer into a flexible pouch in which food or like product is cooked and sterilized. The simulator is a block of polymeric material having a thickness approximately that of a food pouch and a thermal diffusivity generally equal to or slightly above that of food product. A thermal sensor is disposed centrally within the block of polymer material and is connected to electrical leads extending externally of the retort to apparatus that records temperature change as a function of time. A plurality of simulators are placed at various regions in the retort, and the uniformity of the heat transfer under certain operating conditions is determined by measuring the heating rates of the several simulators. Operating conditions, such as flow rates or location of introduction of water, steam and air are changed until a sufficiently uniform heat transfer environment is achieved.

11 Claims, 5 Drawing Figures

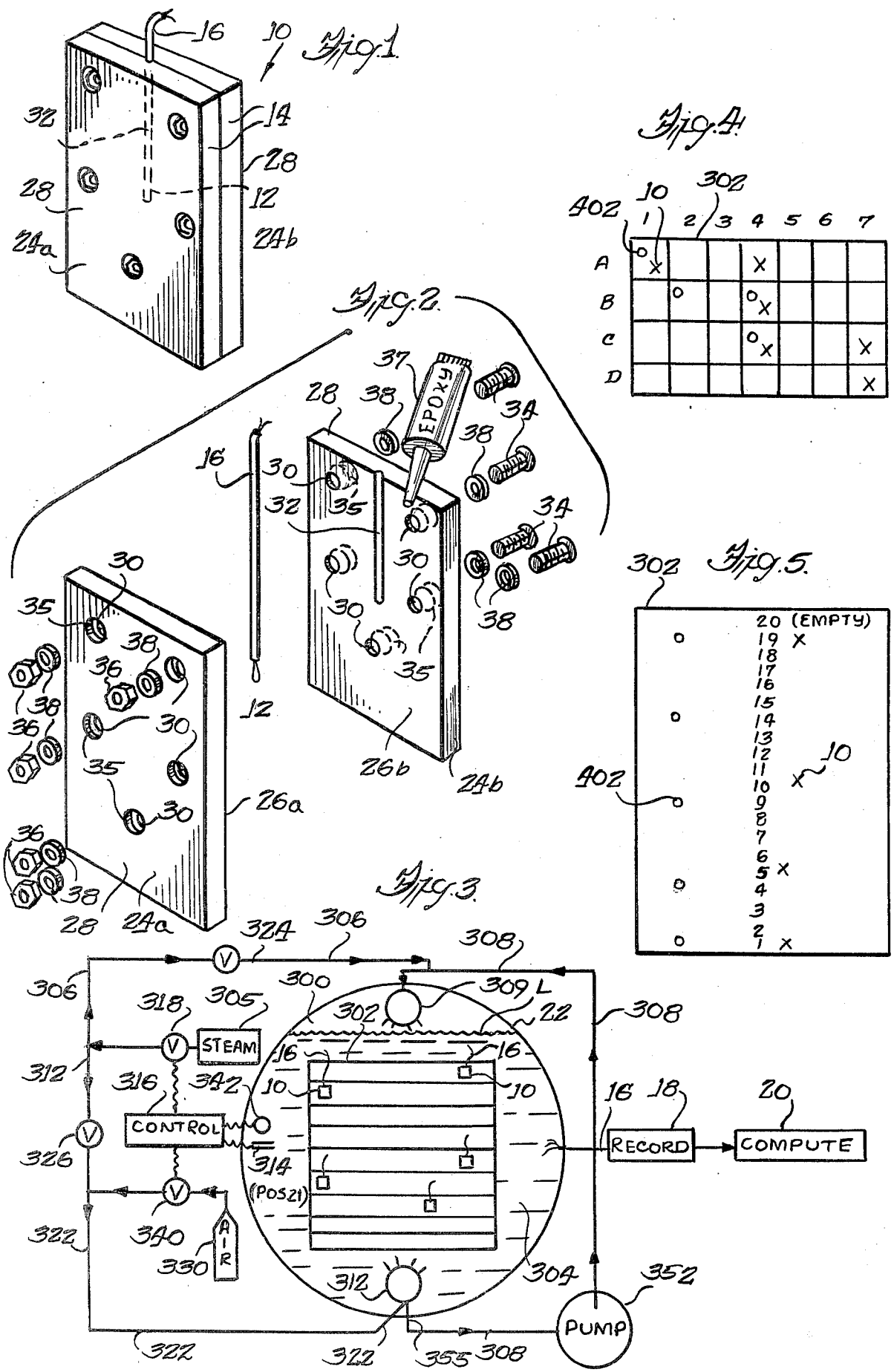

RETORT POUCH THERMAL SIMULATOR AND METHOD OF OPTIMIZING HEAT TRANSFER IN RETORT CONDITIONS

The present invention relates to retort processing of food or the like and more particularly to methods and apparatus for measuring heat transfer in a retort in order to modify the system to assure even heat transfer distribution throughout the system.

BACKGROUND OF THE INVENTION

As an alternative to canning or bottling food products, processed food products may be packaged within a sealed flexible container or pouch and then arranged on racks within a retort where the sealed pouches are subjected to high temperatures to sterilize and/or cook the food product. It is generally necessary to operate the retort at pressures above that of saturated steam at the process temperature in order to generally equalize the pressure of the atmosphere outside the pouches and the pressure within the pouches that develops due to heating of the gases trapped within the pouches and volatilization of water etc. from the product. Equalization of the pressure within and without the pouches reduces stress to the pouches minimizing seam failures that result in product destruction. Pressure equilization is normally accomplished by processing the container submerged in water with overriding air pressure.

More recently, advantages have been appreciated for retorting with a mixture of steam and air, the air being necessary to raise the pressure to above that of saturated steam at the processing temperature. Additional pressure through addition of pressurizing air is achieved at the expense of heat capacity relative to a pure steam atmosphere; however, the reduction of heat capacity can be compensated by increasing the flow rates of steam and air into the retort to achieve adequate heat transfer to the pouches.

It is highly desirable in a retort food processing system that heat transfer to the product within the pouches be uniform at all portions of the retort in order to assure complete cooking and sterilization of the product in all pouches without over heating product within other pouches. Heat transfer is a function of flow rate around a product as well as the temperature of the surrounding environment, and thus, thermal sensors which instantaneously record temperture changes are in themselves insufficient for measuring uniformity of heat transfer. In setting up and periodically checking retort food processing system, it would be desirable to provide apparatus that would simulate a pouch-packaged food product and measure heat transfer thereto. Such apparatus would be useful for measuring heat transfer uniformity in food processing in either a steam-air or a water type retort system where heat transfer in different regions is subject to localized flow conditions.

Several thermal simulators have been developed for measuring heat transferred into food products; however, none of the previously reported designs are truly adaptable or practical for simulating heat transfer into a flexible pouch in a retort for the purpose of measuring heat transfer at various regions. U.S. Pat. No. 3,964,313 describes a thermal simulator in the form of an outer can containing an open celled polymeric matrix uniformly distributing throughout the can a liquid having a predetermined specific gravity. A thermal probe extending to the approximate center of the can is received through a threaded opening at one end of the can. This simulator is used to measure simulated heat transfer into a canned ham or the like.

The simulator described in the U.S. Pat. No. 3,984,313 patent is relatively expensive to produce comprising a number of components. It is also generally unadaptable to simulating heat transfer to a flexible pouch. A flexible pouch normally is quite thin compared to a can for cooking a canned ham, and very little tolerance in centering a thermal probe in a pouch simulator is permissable, whereas slight miscentering of a thermal probe within a larger container has a negligible effect. Substantial difficulties are encountered in precisely centering a thermocouple that is supported from a side of a thin metal can, and if a can type simulator were used, the thermal probe could extend into the can off-center a substantial percentage of the short distance between the opposed sides of a pouch-size container making it impossible to obtain the required uniformity between one simulator and another.

U.S. Pat. No. 4,340,610 describes a thermocouple locator for holding a thermocouple centered inside a flexible pouch that contains a food product to be processed. Although this arrangement is useful for directly measuring the temperature of an actual food sample, the arrangement has substantial disadvantages for measuring heat distribution within a retort. The arrangement is cumbersome and expensive to produce. Furthermore, the outer covering is an actual pouch, and although an actual flexible pouch simulates the actual cooking environment of food, the heat diffusivity to the centered thermocouple will depend on how the flexible pouch folds, bulges, etc., in response to heat, pressure and flowing gases. A container maintaining a uniform distance between the sides and the thermal probe will much more accurately measure the heat exchange provided at different locations within a retort.

Further examples of thermal measuring devices which measure the temperature of food, either directly or through simulation, are found in U.S. Pat. Nos. 1,729,298, 3,690,175, 3,754,465 and 3,812,716.

It is an object of the present invention to provide a device which simulates a food-containing retort pouch both in configuration and in heat diffusivity. It is also an object of this invention to use such a simulator to adjust conditions in a food processing retort.

SUMMARY OF THE INVENTION

In accordance with the present invention a simulator is provided which simulates thermal diffusivity of a flexible retort pouch containing food, the simulator being useful for measuring heat transfer at various locations within a retort chamber where food is heated for sterilization and/or cooking. The simulator comprises a block having a pair broad exterior faces and a thickness between the exterior faces substantially equal to the thickness of a food-filled retort pouch and lateral and longitudinal dimensions substantially greater than the thickness. The block is formed of material that is stable within the wet, high temperature environment of the retort and has a thermal diffusivity of between about 0.005 and about 0.020 in$^2$/min. with a preferred thermal diffusivity range of about 0.010 to about 0.018 in$^2$/min. and a most preferred range of about 0.012 to about 0.015 in$^2$/min. A thermal sensor is embedded in the block precisely centered between the exterior faces, and electrical leads extend from the sensor externally of the block for connection to a temperature recording device.

According to a further aspect of the invention, the block is formed of polymeric material selected from the group consisting of polycarbonate, hard rubber, and silicone rubber.

According to a preferred aspect of the invention, the block comprises a first block half and a second block half each having a complementary interior face and one of the interior faces having a slot extending from an edge generally to its geometric center, the sensor and leads being received in the slot. Means are provided for attaching the block halves together forming a seal between the complementary interior faces.

According to a further aspect, means, are provided for embedding the sensor and electrical leads within the slot, and in particular, a polyurethane epoxy resin fills the slot embedding the sensor and leads and hardening to seal the slot.

According to a further aspect of the invention, the block halves have aligned bores extending between their exterior and interior faces, and bolts extend through the bores and have nuts threaded on the bolts, thereby attaching the block halves together.

A method in accordance with the invention determines optimal operating conditions for a food processing retort. A plurality of food pouch simulators are provided, each having opposed exterior faces, a thickness between the exterior faces generally that of a food-filled flexible retort pouch, a thermal conductivity generally that of a food-filled pouch, and a thermal sensor precisely centered between the opposed exterior faces with electrical leads leading externally of the simulator. The simulators are distributed at various locations within a heating chamber of the retort, and the electrical leads are connected to temperature recording apparatus external of the retort. The retort is operated under a set of operating conditions for a period of time sufficient to achieve generally equilibrium thermal conditions within the retort, and then temperature change within each of the simulators is recorded as a function of time. Heat transfer rates into each simulator are calculated, and uniformity of heat transfer rates into the simulators is evaluated. The steps are repeated with changed retort operating conditions until a desired uniformity of heat transfer at all locations within the chamber is achieved.

Further in accordance with the method, of the retort, operating conditions which are changed to optimize heat transfer uniformity include flow rates of steam, air and water into the chamber and locations of introduction of steam, air and water.

BRIEF DESCRIPTION OF THE DRAWINGS

FIG. 1 is a perspective view, partially cut away, of a thermal simulator embodying various features of the present invention;

FIG. 2 is a perspective assembly view of the device shown in FIG. 1;

FIG. 3 is a diagrammatic view of a water retort having food pouch racks, simulators carried by the pouch racks, and an air, steam and water circulation system for maintaining a pressurized, heated environment within the retort;

FIG. 4 is a diagrammatic representation of the horizontal distribution of simulators within a rack and bare thermal sensors for reference to experiments performed measuring uniformity of heat transfer in the retort apparatus of FIG. 3; and FIG. 5 is a diagrammatic representation of vertical layers within the rack of FIG. 4 for reference to the performed experiments.

DETAILED DESCRIPTION OF THE PRESENT INVENTION

In accordance with the present invention a simulator 10 is provided which approximates the heat diffusivity of food within a flexible retort pouch. The simulator 10 consists of a thermal sensor 12 centrally disposed within a block 14 formed of polymeric material that has a thickness typical of a flexible retort pouch and which has a thermal diffusivity approximating that of food which will typically be processed within the retort pouch. Electrical leads 16 from the sensor 12 extend externally of the block and externally of a retort 22 (FIG. 3) to recording apparatus 18. Computing apparatus 20 is preferably employed to relate measured temperatures to meaningful thermal parameters, such as heating rate ($f_h$). A plurality of simulators 10 distributed throughout the retort (FIG. 3) indicate the uniformity of the heat exchange environment at various regions within the retort 22 during operating conditions.

A preferred block 14 consists of two separate block halves 24a, 24b bolted or otherwise secured together. One block half 24a (hereinafter referred to as the plain block half) has a flat interior face 26a that is uninterrupted except for bolt bores 30 extending between its interior face and its exterior face 28. The other block half 24b (hereinafter referred to as the slotted block half) has a flat interior face 26b interrupted by bolt bores 30 as well as by an elongated slot 32 leading from one lateral edge to the geometric center. Both of the block halves are configured as rectangular prisms with identical lateral and longitudinal dimensions; however, the slotted block half 24b is thicker than the plain block half 24a by the depth of the slot 32, providing that when the block halves are secured together by nuts 36 and bolts 34 with their interior faces 26 pressed against each other, the slot 32 provides a passageway to the exact geometric center of the block.

To simulate the thermal diffusivity of a food-containing retort pouch, the geometry of the block 14 approximates that of the food pouch in having a thickness generally equal to that of a food-containing pouch and lateral and longitudinal dimensions substantially greater than its thickness. It is not considered particularly important that the longitudinal and lateral dimensions of the block 14 simulate that of the food pouch so long as those dimensions are significantly greater than the thickness, so that heat will diffuse to the center of the block 14 primarily from its broad exterior faces 28.

By way of example, the simulator 10 includes a plain block half 24a and a slotted block half 24b with longitudinal and lateral dimensions of 4.50 in. and 3.25 in. respectively. The plain block half 24a is 0.420 in. thick, whereas the slotted block half 24b is 0.480 in. thick having a slot 0.060 in. deep and 0.09 in. wide. The total thickness of the block, therefore is 0.900 in.

The block halves 24a,b are attached together by means of broad-headed bolts 34 which extend through the bolt bores of the facing block halves and nuts 36. Preferably, the bolt bores 30 include a countersunk portion 35 for receiving the bolt heads 40, nuts 36 and washers 38. The countersunk portion 35 is broader than the nuts 36 and heads of the bolts 34 providing some play to allow for thermal expansion. Stainless steel bolts 34 and nuts 36 may be used to join the block halves 24 together as stainless steel can withstand the somewhat corrosive environment of the interior of the retort 22. Alternatively, plastic nuts and bolts might be used, plastic bolts minimizing the thermal transfer of heat through the bolts 34 to the interior of the blocks 14. However, the bolt bores 30 are sufficiently remote from the sensor 12, i.e., at least about one block thickness, so that even metal bolts do not seriously affect heat transfer to the region of the sensor 12. In the illustrated embodiment, a pattern of five bolt bores 30 is provided in each block half 24, the bolt bores being arranged along the slot 32 so as to insure good interfacial sealing of the block halves 24 in the region of the slot.

A tiny thermocouple sensor 12, e.g. formed of type T, copper constantan, 24 gauge thermocouple wire, is disposed at the inner end of the slot 32 prior to joining the block halves 24, and the thermocouple and electrical leads 16 extending therefrom are embedded in a fluid resin 37, such as polyurethane epoxy resin, which solidifies to seal the passageway provided by the slot 32 after the block halves 24 have been joined. Should the embedded thermocouple sensor 12 wear out, the block halves 24 may be unbolted and separated and the hardened resin 37 and embedded thermocouple sensor removed from the slot. The resin 37 preferably has a lower heat diffusivity than the polymeric material of which the block halves 24 are formed, and the electrical leads 16 extending through the slot 32 are thin and covered with an insulating material, e.g., extruded polytetrafluoroethylene; thus, heat transfer through the narrow slot 32 to the thermocouple sensor 12 is minimized.

The block halves 24 are formed of a polymeric material capable of withstanding the conditions within the retort 22 and having a thermal diffusivity approximating that of foods to be processed, but preferably slightly higher than that of foods. (Thermal diffusivity (k) of a material, as defined by C. R. Stumbo *Thermobacteriology in Food Processing*, 2nd ed. Academic Press 1973 p. 194.

$$k = \frac{\text{thermal conductivity}}{\text{specific heat} \times \text{density}})$$

A bare thermocouple sensor or a thermocouple sensor embedded in material having a very high thermal diffusivity relative to food product would not be suitable for measuring heat exchange because such probes would merely measure temperature which might be generally uniform throughout the retort 22 even if heat transfer at various regions are not uniform due to differing circulation within the retort.

Foods which are commonly processed in retort pouches generally having thermal diffusivities ranging from about 0.010 in$^2$/min. to about 0.012 in$^2$/min., and a polymeric material having a thermal diffusivity within this range is suitable; however, it is preferred that the thermal diffusivity of the polymeric material be slightly higher than that of the food it simulates so that it is slightly more sensitive to heat exchange differences than is the food.

The most sensitive material for measuring differences in heat transfer environment would be a material, such as a metal, having a very high thermal diffusivity and absorbing heat rapidly from the environment. Such material registers a high percentage difference in heating time between a low heat transfer environment and a high heat transfer environment. An insulating material, on the other hand, would register a very small percentage difference in heating time in different heat transfer environments. High thermal diffusivity materials, however, are unsuitable for measuring heat transfer uniformity within a sealed retort where a heating lag is required so that heating rate can still be measured as a function of thermal change within the simulator after the surrounding retort chamber environment has generally reached thermal equilibrium conditions. If a retort pouch thermal simulator has a thermal diffusivity slightly greater than that of a food product, differences in heat transfer that affect the heating rate in a simulator would also be of concern with a food product. Differences that are not detected because the limiting factor becomes the thermal diffusivity of the simulator, would not affect a food product. Thus, the polymer should have a thermal diffusivity of between about 0.005 and about 0.020 in$^2$/min. A preferred thermal diffusivity for the polymer is between about 0.010 to about 0.018 in$^2$/min. and most preferably between about 0.012 and about 0.015 in$^2$/min.

A particularly suitable polymer is a polycarbonate resin such as that sold as GE Lexan polycarbonate resin. This resin is stable at the operating temperatures of a retort, i.e., up to about 250° F., has a thermal diffusivity of about 0.013 in$^2$/min and is sufficiently rigid to be formed by machining. The polycarbonate polymer is rigid but can be machined to provide smooth interior faces 26 that self seal with each other when held under compression by the connecting nuts 36 and bolts 34. Other suitable materials for forming the block halves 24 include hard rubber and silicone rubber.

When rigid materials, such as polycarbonate, are used to form the block halves, machining is the preferred method of forming the block halves 24 as this provides the best assurance that their interior faces 26 have sufficient flatness to self seal. If more flexible material, such as silicone rubber, is used to form the block halves 24, the block halves may be molded because any irregularities of the interior faces 26 due to shrinkage during cooling or setting is compensated by the resiliency of the polymeric material.

Illustrated in FIG. 3 is a retort 22 for food processing in which thermal sensors might be used. The retort 22 is a cylindrical boiler having a cylindrical chamber 300 in which a rack 302 is inserted by means of rails (not shown). The rack 302 either carries an array of pouches suspended vertically or pouches disposed horizontally in trays.

The illustrated retort 22 is a water retort where the rack 302 is totally submerged in water 304 at a level L. The water is heated by steam which is introduced from a source 305 either via conduit 306 along with recirculating water in conduit 308 through a top spreader 309, which is an elongated, multiply apertured pipe extending in an axial direction above the water level L in the retort chamber 300, or is introduced through a bottom spreader 312, which is likewise a multiply apertured pipe extending in an axial direction. Steam is introduced into the chamber 300 according to a measured temperature at a retort thermometer 314 extending into the water 304 through the side of the retort at position 21. The thermometer 314 is connected to a control unit 316 which opens a valve 318 to admit a required amount of steam from the source 305. The choice of introduction of steam via the conduit 306 through the top spreader 309 or via a conduit 322 through the bottom spreader 312 is controlled by opening the appropriate manual valve, 324, or 326 respectively.

Air from a source 330 is introduced via the conduit 322 to the bottom spreader 312 where it is bubbled through the water 304. The required amount of air needed to maintain the desired pressure above that of the saturated steam pressure at the operating temperature is admitted through a valve 340 that is actuated by the control unit 316 according to the pressure detected by a gauge 342 within the retort chamber 300.

The flow of water is primarily created by recirculation of water through the recirculation conduit 308, a pump 352 being used to draw water through a drain 355 at the bottom of the retort 22 and reinforcing the water through the top spreader 309. Contributing to the circulation in the tank is the air introduced through the bottom spreader 312, and if air is continually supplied to the chamber 300 and bled from the chamber, the air flow itself can create substantial water circulation within the chamber 300.

Use of sensors 10 according to the invention to achieve retort conditions that assure uniform heat exchange to retort pouches in all portions of a retort, such as that illustrated in FIG. 3, will now be illustrated by way of example.

A plurality of sensors 10 are distributed throughout a retort. The retort has a cylindrical processing chamber 400, with a rectangular rack array in which pouch simulator positions are represented as X's in FIGS. 4 and 5, FIG. 4 showing an array of horizontal pouch positions in the rack and FIG. 5 showing vertical levels within the rack. Bare thermocouples 402 (represented as O's in FIGS. 4 and 5), are disposed within the chamber at the following positions represented by horizontal and vertical coordinates:

| No. | Horizontal Position in Rack | Vertical Level | No. | Horizontal Position in Rack | Vertical Level |
|---|---|---|---|---|---|
| 1 | A1 | 1 | 11 | B4 | 9 |
| 2 | B2 | 1 | 12 | C4 | 9 |
| 3 | B4 | 1 | 13 | A1 | 14 |
| 4 | C4 | 1 | 14 | B2 | 14 |
| 5 | A1 | 4 | 15 | B4 | 14 |
| 6 | B2 | 4 | 16 | C4 | 14 |
| 7 | B4 | 4 | 17 | A1 | 19 |
| 8 | C4 | 4 | 18 | B2 | 19 |
| 9 | A1 | 9 | 19 | B4 | 19 |
| 10 | B2 | 9 | 20 | C4 | 19 |

In addition, the retort thermometer 314, position 21, FIG. 3.

Simulators 10 are disposed within the chamber at the following positions:

| No | Horizontal Position in Rack | Vertical Level | No. | Horizontal Position in Rack | Vertical Level |
|---|---|---|---|---|---|
| 24 | C2 | 10 | | | |
| 25 | A1 | 1 | 37 | A1 | 10 |
| 26 | A4 | 1 | 38 | A4 | 10 |
| 27 | B4 | 1 | 39 | B4 | 10 |
| 28 | C4 | 1 | 40 | C4 | 10 |
| 29 | C7 | 1 | 41 | C7 | 10 |
| 30 | D7 | 1 | 42 | D7 | 10 |
| 31 | A1 | 5 | 43 | A1 | 19 |
| 32 | A4 | 5 | 44 | A4 | 19 |
| 33 | B4 | 5 | 45 | B4 | 19 |
| 34 | C4 | 5 | 46 | C4 | 19 |
| 35 | C7 | 5 | 47 | C7 | 19 |
| 36 | D7 | 5 | 48 | D7 | 19 |

The bare thermocouples 402 measure the temperature at each point while the simulators 10 measure the heating rate from the environment within the retort chamber 400 to the thermocouple sensors 12 within the blocks 14.

Measurement of heating rate ($f_h$) (in minutes), which is a function of heat diffusivity of the sensor blocks 14, are calculated from the measured temperatures of the sensors 12 within the blocks 14 as the temperatures change as a function of time. The calculation is described in Stumbo supra. pp. 129-142, and the calculation is incorporated herein by reference. The calculations are preferably automatically carried out by the computing apparatus 20 the thermal sensors with the data collected by and recorded by the recording apparatus 18.

Experiments 1 and 2 are conducted in vertical racks that are empty except for the simulators, the substantially empty retort representing ideal flow conditions. Experiments 3-10 are conducted in horizontal racks with the positions filled with flexible pouches unless occupied with simulators 10.

The retort conditions for the ten experiments are as follows:

1. Steam is introduced through the bottom spreader, water in the 400 gal. retort is recirculated at a rate of about 300 gal. per minute.
2. Steam is introduced through the bottom spreader, water in the 400 gal. retort is recirculated at a rate of about 300 gal. per minute.
3. Steam is introduced through the bottom spreader; water is recirculated at a rate of about 300 gal. per minute.
4. Steam is introduced through the bottom spreader; water is recirculated at a rate of about 125 gal. per minute.
5. Steam is introduced through the bottom spreader; water is recirculated at a rate of about 50 gal. per minute.
6. Water is not recirculated. Air and steam are introduced through the bottom spreader and air is bled from above the water level, the agitating air being relied upon to provide the circulation in the retort chamber.
7. Steam is introduced along with recirculated water through the top spreader; water is recirculated at a rate of about 300 gal. per minute.
8. Steam is introduced along with water through the top spreader; water is recirculated at a rate of about 125 gal. per minute.
9. Steam is introduced along with water through the top spreader; water is recirculated at a rate of about 50 gal. per minute.
10. Water is not recirculated. Air and steam are introduced through the bottom spreader and air is bled from above the water level, the agitating air being relied upon to provide the circulation in the retort chamber.

From the thermocouple data (not shown in detail) the following conclusions were made:

The raw data of measured heating rate for the ten experiments is given below:

| Point No. | 1 | 2 | 3 | 4 | 5 |
|---|---|---|---|---|---|
| 24 | 12.29 | 12.57 | 13.26 | 15.63 | 15.51 |
| 25 | 12.48 | 12.69 | 12.94 | 13.68 | 13.22 |
| 26 | 12.49 | 12.82 | 12.97 | 13.72 | 13.64 |
| 27 | 12.23 | 12.65 | 12.91 | 13.29 | 13.75 |
| 28 | 12.49 | 12.73 | 13.17 | 13.79 | 14.27 |

-continued

| | | | | | |
|---|---|---|---|---|---|
| 29 | 12.48 | 12.62 | 13.65 | 14.73 | 14.19 |
| 30 | 12.43 | 12.61 | 13.19 | 14.23 | 14.22 |
| 31 | 12.28 | 12.59 | 14.04 | 14.29 | 13.70 |
| 32 | 12.28 | 12.57 | 12.82 | 14.03 | 14.27 |
| 33 | 12.48 | 12.83 | 12.98 | 13.98 | 14.53 |
| 34 | 12.79 | 12.81 | 12.93 | 14.18 | 14.66 |
| 35 | 12.53 | 12.78 | 13.41 | 14.28 | 14.56 |
| 36 | 12.74 | 12.79 | 15.10 | 13.54 | 14.56 |
| 37 | 12.50 | 12.76 | 13.27 | 14.96 | 14.84 |
| 38 | 12.56 | 12.79 | 13.38 | 13.95 | 14.46 |
| 39 | 12.51 | 12.74 | 13.61 | 13.53 | 14.89 |
| 40 | 12.48 | 12.80 | 13.03 | 13.92 | 15.17 |
| 41 | 12.69 | 12.96 | 13.57 | 14.09 | 14.58 |
| 42 | 12.51 | 12.89 | 14.16 | 13.53 | 14.84 |
| 43 | 12.67 | 12.90 | 13.17 | 13.59 | 13.38 |
| 44 | 12.71 | 12.80 | 12.65 | 13.30 | 13.59 |
| 45 | 12.93 | 13.00 | 12.89 | 13.40 | 14.19 |
| 46 | 12.80 | 12.83 | 12.98 | 13.43 | 14.11 |
| 47 | 12.82 | 13.03 | 12.90 | 13.29 | 13.71 |
| 48 | 12.85 | 12.96 | 12.49 | 13.66 | 14.35 |

| Point No | 6 | 7 | 8 | 9 | 10 |
|---|---|---|---|---|---|
| 24 | 14.23 | 13.38 | 13.83 | 14.42 | 14.22 |
| 25 | 14.17 | 13.44 | 13.71 | 12.66 | 13.96 |
| 26 | 13.16 | 13.52 | 13.80 | 14.59 | 13.18 |
| 27 | 13.53 | 13.52 | 14.13 | 15.17 | 12.92 |
| 28 | 13.34 | 13.23 | 13.82 | 14.69 | 12.74 |
| 29 | 14.91 | 13.39 | 13.88 | 14.68 | 13.77 |
| 30 | 14.16 | 12.94 | 13.79 | 14.72 | 13.61 |
| 31 | 14.25 | 13.28 | 13.73 | 13.50 | 14.19 |
| 32 | 13.51 | 13.59 | 13.80 | 15.40 | 13.13 |
| 33 | 13.52 | 13.65 | 14.27 | 15.07 | 13.28 |
| 34 | 13.61 | 13.41 | 14.58 | 14.74 | 13.06 |
| 35 | 14.24 | 13.40 | 13.77 | 14.35 | 14.18 |
| 36 | 13.89 | 13.23 | 14.18 | 13.97 | 14.82 |
| 37 | 14.17 | 13.52 | 13.91 | 13.44 | 14.29 |
| 38 | 13.75 | 13.38 | 13.84 | 15.32 | 13.16 |
| 39 | 13.42 | 13.38 | 14.02 | 15.48 | 13.21 |
| 40 | 13.45 | 13.40 | 14.29 | 15.09 | 13.50 |
| 41 | 14.47 | 13.67 | 13.68 | 14.56 | 14.48 |
| 42 | 14.32 | 13.10 | 13.63 | 14.28 | 14.40 |
| 43 | 14.21 | 12.89 | 12.98 | 12.88 | 13.74 |
| 44 | 13.59 | 13.27 | 13.72 | 14.02 | 13.90 |
| 45 | 13.70 | 12.79 | 13.37 | 13.96 | 13.16 |
| 46 | 13.44 | 12.56 | 12.93 | 13.59 | 13.25 |
| 47 | 13.81 | 13.00 | 13.40 | 14.07 | 13.44 |
| 48 | 13.68 | 13.07 | 13.44 | 13.54 | 13.91 |

The heating rate data is summarized in the following table:

| | | Testing | | | |
|---|---|---|---|---|---|
| Test | Maximum | Minimum | Range | *Range-1 | Average |
| 1 | 12.93 | 12.23 | .70 | .59 | 12.57 |
| 2 | 12.57 | 13.03 | .47 | .43 | 12.78 |
| 3 | 15.10 | 12.49 | 2.61 | 1.67 | 13.35 |
| 4 | 15.63 | 13.29 | 2.33 | 1.67 | 13.92 |
| 5 | 15.51 | 13.22 | 2.29 | 1.95 | 14.29 |
| 6 | 14.47 | 13.17 | 1.31 | 1.14 | 13.97 |
| 7 | 13.67 | 12.56 | 1.11 | 0.88 | 13.32 |
| 8 | 14.29 | 12.93 | 1.36 | 1.25 | 13.78 |
| 9 | 15.48 | 12.66 | 2.82 | 2.60 | 14.33 |
| 10 | 14.82 | 12.74 | 2.08 | 1.74 | 13.64 |

*Range after removing highest or lowest value most different than next high or low valve.

This summary shows that although in no case did the uniformity of heating rate in the pouch-filled retort achieve the uniformity of heating rates achieved in the substantially empty retort, the range of heating rates at various points could be narrowed by adjusting various conditions of the system including flow rates of air and steam and location of air and steam introduction.

The required speed at which the temperatures in the regions of the rack achieve substantial equality after the retort is brought up to operating temperature and the required degree of uniformity of the heat transfer throughout the retort depends on the product being retorted. Generally, the temperatures within the rack regions of the retort should be brought to within about 2° F. within 5 minutes. Using pouch simulators having thermal diffusivities between 0.010 and 0.018 and thicknesses of between about 0.75 and about 1.50 inches, the heating rates at all points should not vary more than about 1.5 min.

Based on the data obtained for the particular experimental system, it was concluded that temperature and heat exchange uniformities were unsatisfactory when water was recirculated from top to bottom with steam introduced through the bottom spreader.

As would be expected, heating rates were higher and spread of heating rates lowest at higher recirculation rates. When steam was added to the water being recirculated from top to bottom at 300 gal/min, all temperatures in the water were within a 2° F. range within three minutes of when the retort reached operating temperature (as determined by the thermometer) and within a 1° F. range within six minutes, and heat exchange uniformity was satisfactory. When steam was added to the water being recirculated from top to bottom at 125 gal/min, temperature distribution and heat exchange uniformity were borderline, temperatures throughout the retort falling within a 2° F. range within six minutes and within a 1° F. range in 9 minutes. At a recirculation rate of 50 gal/min it took twelve minutes to bring the temperature range to within 2° F.

Temperature and heat transfer distributions were borderline when steam and agitating air were introduced through the bottom spreader and water was not recirculated.

While the invention has been described with respect to certain preferred embodiments, modifications obvious to one with ordinary skill in the art may be made without departing from the scope of the invention.

Various features of the invention are recited in the following claims.

What is claimed:

1. A simulator of thermal diffusivity of a flexible retort pouch containing a food product, which simulator is useful for measuring heat transfer at various locations within a retort chamber where food is heated for sterilization and/or cooking, the simulator comprising,
    a block formed of material that is stable within the wet, heated environment of the retort and having a thermal diffusivity of between about 0.005 in$^2$min. and about 0.20 in$^2$/min.
    said block having a pair of broad exterior faces and a thickness as measured between said exterior faces substantially equal to the thickness of a food-filled retort pouch and lateral and longitudinal dimensions substantially greater than the thickness,
    a thermal sensor embedded in said block precisely centered midway between said exterior faces, and
    electrical leads extending from said sensor externally of said block, said leads being connectable to a temperature recording device.

2. A simulator according to claim 1 wherein said block is formed of polymeric material selected from the group consisting of polycarbonate, hard rubber, and silicone rubber.

3. A simulator according to claim 1 wherein said block comprises a first block half and a second block half, each block half having a complementary interior face, one of said interior block faces having a slot extending from an edge generally to its geometric center wherein said sensor and electrical leads are received, and means for attaching said block halves together forming a seal between said complementary interior faces.

4. A simulator according to claim 3 including material embedding said sensor and said electrical leads within said slot.

5. A simulator according to claim 4 wherein said embedding material is a polyurethane epoxy resin which hardens to seal said slot.

6. A simulator according to claim 3, said block halves having aligned bores extending between their exterior and interior faces, said attaching means comprising bolts extending through said bores and nuts threaded onto said bolts.

7. A simulator according to claim 1, said material having a thermal diffusivity of between about 0.010 in$^2$/min. and about 0.018 in$^2$/min.

8. A simulator according to claim 1, said material having a thermal diffusivity of between about 0.012 in$^2$/min and about 0.015 in$^2$/min.

9. A method of determining optimal operating conditions for a food processing retort comprising
providing a plurality of food pouch simulators, each simulator having opposed exterior faces and a thickness between said exterior faces generally that of a food-filled flexible pouch and a thermal conductivity generally that of a food-filled pouch, a thermal sensor precisely centered between said opposed exterior faces, and electrical leads extending externally of said simulator,
distributing said simulators at various locations within a heating chamber of said retort,
connecting said leads to temperature recording apparatus external of the retort,
operating said retort under a set of operating conditions for a period of time sufficient to achieve generally equilibrium conditions within said retort,
recording temperature change within each of said simulators as a function of time,
calculating heat transfer rates into each of said sensors,
evaluating the equality of heat transfer rates at the various locations within said retort, and
repeating the above steps with changed operating conditions until a desired uniformity of heat transfer rates at all locations within said chamber is achieved.

10. A method according to claim 9 wherein the operating conditions which are changed to optimize heat transfer uniformity include the flow rates of steam, air and water into said retort.

11. A method according to claim 9 wherein operating conditions which are changed to optimize heat transfer uniformity include the locations of introduction of steam, air and water into said retort.

* * * * *